United States Patent
Casarcia et al.

(10) Patent No.: US 6,696,830 B2
(45) Date of Patent: Feb. 24, 2004

(54) METHOD AND INSPECTION STANDARD FOR EDDY CURRENT INSPECTION

(75) Inventors: Dominick A. Casarcia, Osgood, IN (US); Douglas E. Ingram, Cincinnati, OH (US); William S. McKnight, Fairfield, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/683,697

(22) Filed: Feb. 5, 2002

(65) Prior Publication Data

US 2003/0146745 A1 Aug. 7, 2003

(51) Int. Cl.[7] .......................... G01R 35/00; G01N 27/72
(52) U.S. Cl. ....................................... 324/202; 324/219
(58) Field of Search ................................ 324/202, 237, 324/238, 240, 225, 219; 702/35, 38

(56) References Cited

U.S. PATENT DOCUMENTS

| | | | |
|---|---|---|---|
| 3,963,949 A | | 6/1976 | Church |
| 4,418,315 A | * | 11/1983 | Edwards et al. ............ 324/202 |
| 4,814,703 A | * | 3/1989 | Carr et al. .................. 324/207 |
| 4,922,201 A | * | 5/1990 | Vernon et al. .............. 324/236 |
| 5,006,801 A | | 4/1991 | Young |
| 5,175,498 A | | 12/1992 | Cueman et al. |
| 5,262,722 A | | 11/1993 | Hedengren et al. |
| 5,315,234 A | * | 5/1994 | Sutton, Jr. et al. .......... 324/242 |
| 5,418,823 A | | 5/1995 | Kervinen et al. |
| 5,442,286 A | * | 8/1995 | Sutton, Jr. et al. .......... 324/242 |
| 5,483,160 A | * | 1/1996 | Gulliver et al. ............. 324/242 |
| 5,717,332 A | | 2/1998 | Hedengren et al. |
| 6,339,326 B1 | * | 1/2002 | Trantow ..................... 324/219 |
| 6,356,069 B1 | * | 3/2002 | Trantow et al. ............. 324/202 |
| 6,469,503 B2 | * | 10/2002 | Trantow et al. ............. 324/219 |

* cited by examiner

Primary Examiner—John Barlow
Assistant Examiner—Toan M Le
(74) Attorney, Agent, or Firm—Nathan Herkamp; Armstrong Teasdale LLP; Robert B. Reeser, II

(57) ABSTRACT

A method for inspecting a metallic component comprises providing an inspection standard having an eddy current signature substantially similar to an eddy current signature of the metallic component, wherein the inspection standard body is fabricated from a non-metallic material. The method also comprises inspecting the metallic component with an eddy current probe with reference to the inspection standard.

20 Claims, 4 Drawing Sheets

METHOD AND INSPECTION STANDARD FOR EDDY CURRENT INSPECTION

FEDERAL RESEARCH STATEMENT

The government has rights in this invention pursuant to Contract No. F33657-99-D-2050 awarded by the Department of the Air Force.

BACKGROUND OF INVENTION

The present invention relates generally to the inspection of structures by employing non-destructive techniques and, more particularly, to a method and an inspection standard for eddy current inspections.

The safety and structural integrity of aircraft is a concern to manufacturers as well as consumers. As the average age of aircraft in service grows, reliable and accurate inspections of aircraft components become increasingly important. For example, non-destructive inspections may be the only means available to identify deteriorating areas of an exterior surface of the aircraft and associated surface fastener openings. Furthermore, it is common to detect cracks or other defects located below the aircraft surface using non-destructive methods.

Eddy current inspection is a commonly used non-destructive inspection means used to detect discontinuities or flaws in the surfaces of various components, including aircraft engine components and aircraft skin surfaces. Generally, eddy current inspection is based on the principle of electromagnetic induction. In at least one known method, a drive coil is used to induce eddy currents within a conductive material that is being inspected. Secondary magnetic fields that may result from the eddy currents are detected by a sense coil which generates signals that are subsequently processed for the purpose of detecting flaws.

Eddy current testing for flaws in materials is typically done by mechanically scanning a single probe in at least two dimensions. For example, U.S. Pat. No. 5,345,514, entitled "An Improved Method for Inspecting Components Having Complex Geometric Shapes" and assigned to The General Electric Company describes methods for interpreting eddy current image data acquired by a single probe, particularly in the context of inspecting a high pressure turbine (HPT) disk dovetail slot. Such inspection instruments are capable of detecting cracks and other deformations in a workpiece by measuring the eddy current induced in the workpiece.

The term eddy current, as generally understood in the art and as used herein, refers to a current created or induced in a material by an applied varying magnetic field, or by moving the material in a magnetic field. Suitable electronics for acquiring data from an eddy current inspection are disclosed in U.S. Pat. No. 5,182,513, entitled "Method and Apparatus for a Multi-Channel Multi-Frequency Data Acquisition System for Nondestructive Eddy Current Inspection Testing" and assigned to The General Electric Company.

At least some known systems for performing eddy current inspections include a master or standard component (hereinafter "standard") which is believed to be structurally sound. The standard has an eddy current signature which is determined by performing an eddy current inspection of the standard. An eddy current inspection of a component to be inspected (suspect component) is performed to obtain an eddy current signature of the suspect component, and, the signatures are compared to determine whether the suspect component is structurally sound. Standards are especially useful in field inspections where process drift and differing environments may generate erroneous results when using a pre-calibrated scanning electronics. Therefore, in field inspections, it is sometimes useful to calibrate the scanning electronics using an eddy current signature of a standard as a reference. The standard is typically an actual component that is fabricated from the same material as the suspect component. Accordingly, when the suspect component is expensive and/or heavy, the standard is typically also expensive and/or heavy which may result in additional expenses and/or difficulty in handling.

SUMMARY OF INVENTION

In one aspect, a method for inspecting a metallic component is provided. The method comprises providing an inspection standard having a body shaped substantially similar to a body of the metallic component, wherein the inspection standard body is fabricated from a non-metallic material. The method also comprises inspecting the metallic component with an eddy current probe with reference to the inspection standard.

In another aspect, an inspection standard is provided. The inspection standard comprises a body fabricated from a non-metallic material and having at least one surface. A plurality of grooves extends across the outer surface and inner surface. The inspection standard also comprises a conductor positioned within each of the In a further aspect, an inspection device comprises an inspection standard having a non-metallic body and an inspection device comprising a probe, wherein the probe is in close proximity to the inspection standard.

DETAILED DESCRIPTION

Figure 1:
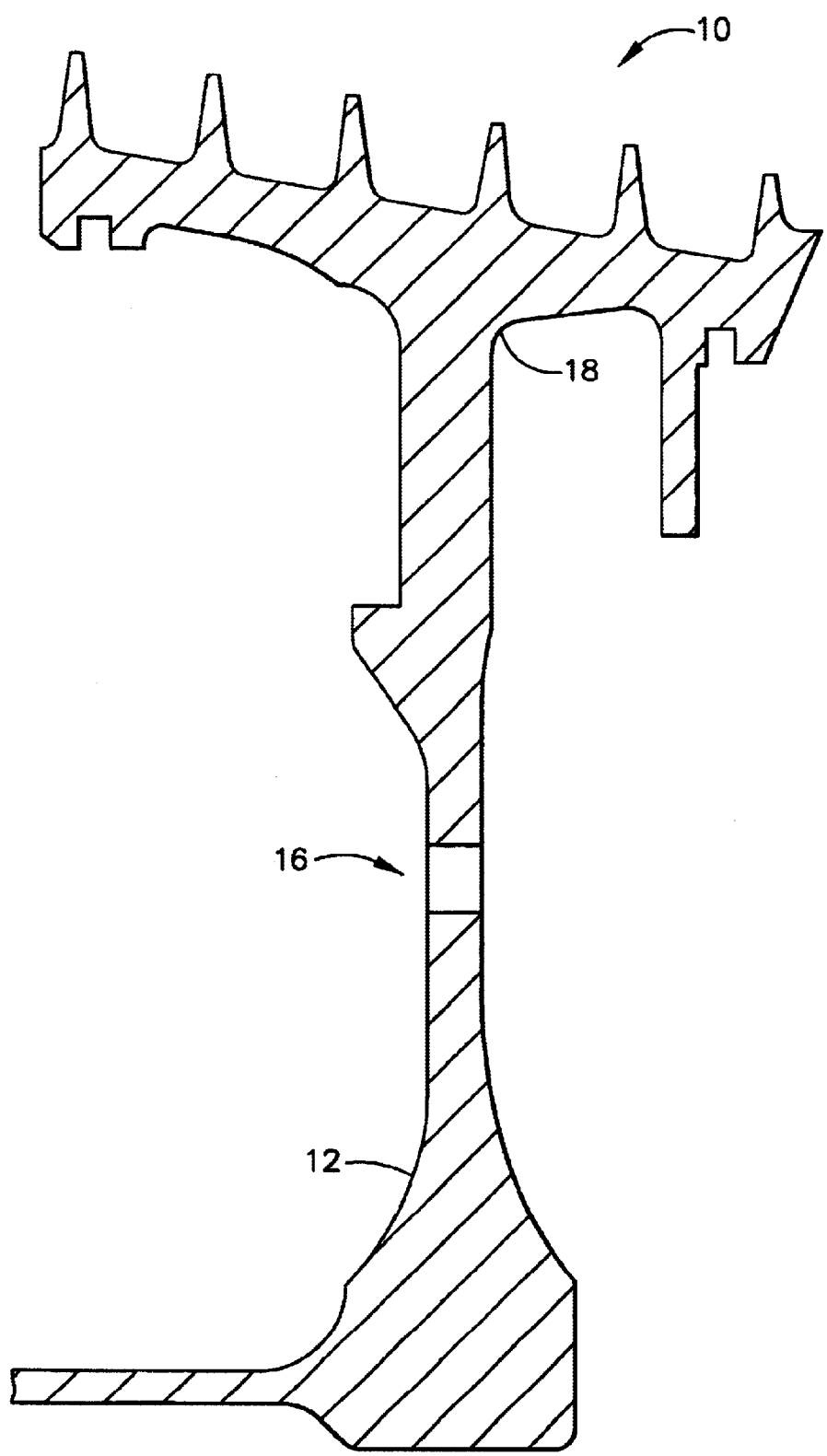
FIG. 1 is side view of a generic component to be inspected.

FIG. 1 is a perspective view of a generic component 10 to be inspected for defects. Component 10 includes at least a plurality of prismatic geometric surfaces and at least one surface 12. Component 10 also includes at least one opening 16 and at least one fillet 18. Component 10 is used for illustrative purposes only and it is contemplated that the benefits of the invention accrue to components which have various prismatic geometric surfaces and features such as, but not limited to, fillets, openings, holes, corners, and interior voids.

Figure 2:
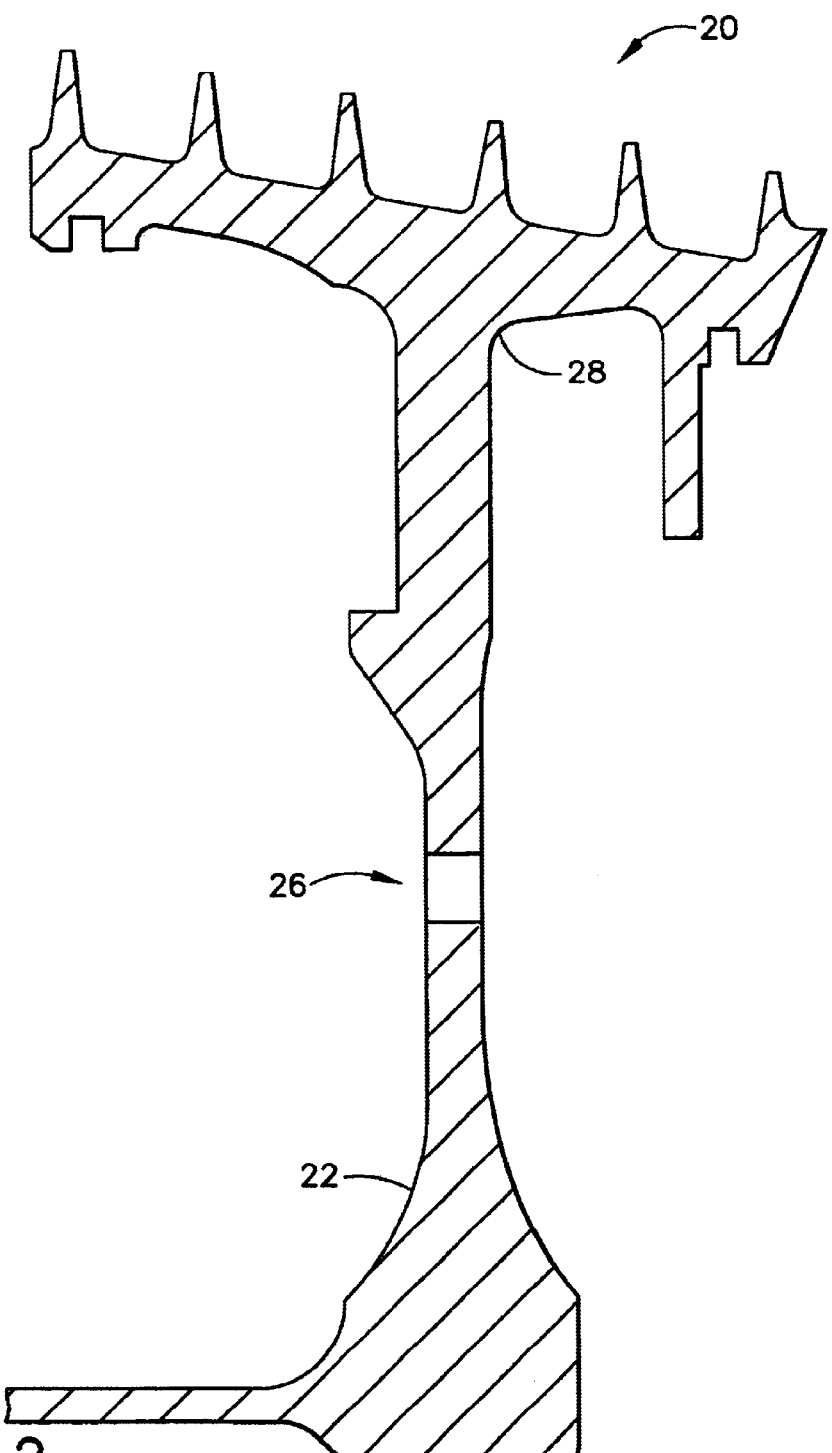
FIG. 2 is a side view of a known standard.

FIG. 2 is a perspective view of a known standard 20 that is representative of component 10 (shown in FIG. 1). Standard 20 includes at least a plurality of prismatic geometric surfaces and at least one surface 22. Standard 20 also includes at least one opening 26 and at least one fillet 28. Standard 20 and component 10 are fabricated from the same material and have a substantially similar signature.

Figure 3:
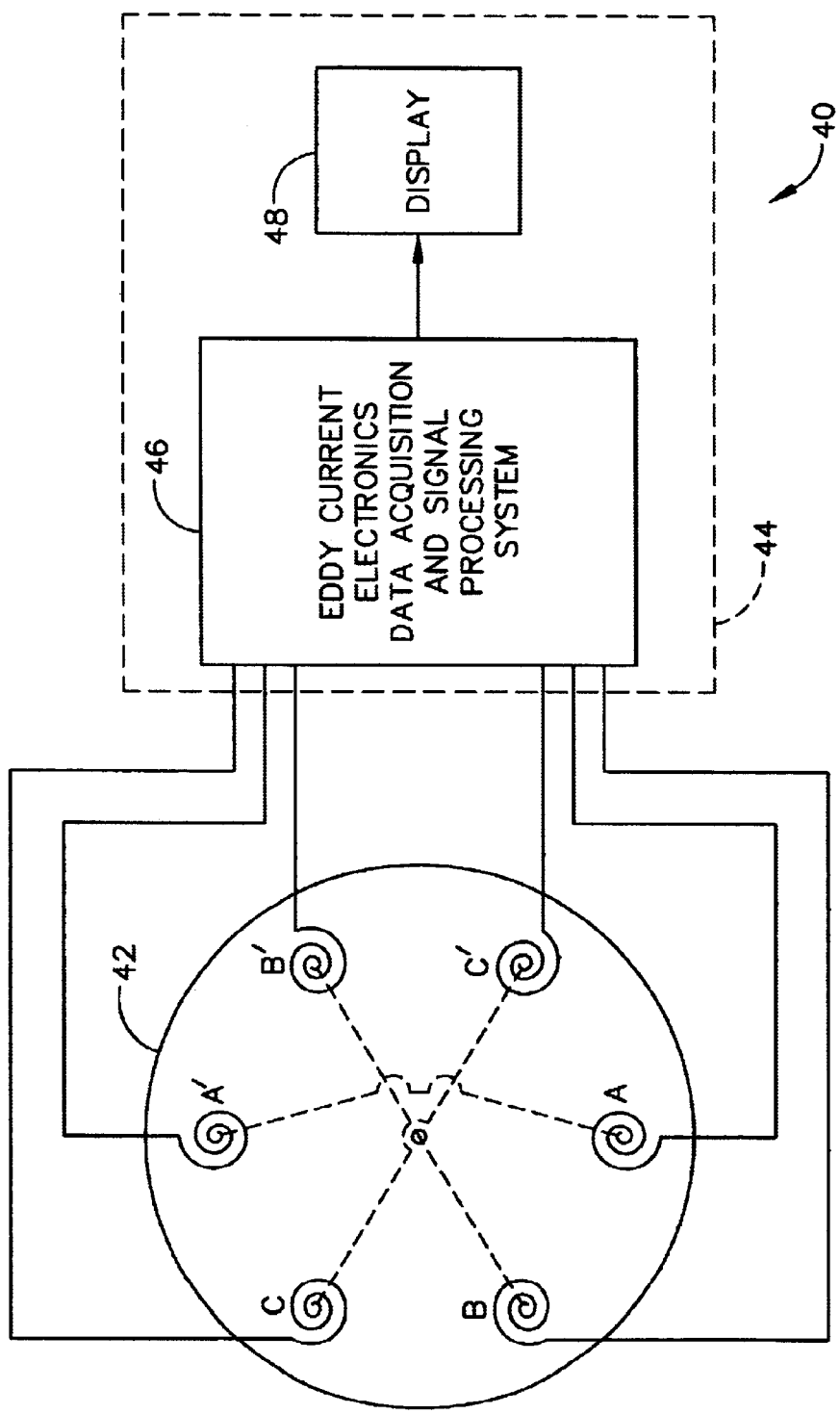
FIG. 3 is plan view of a known eddy current inspection device.

FIG. 3 is plan view of a known eddy current inspection device 40 including an eddy current probe 42 connected to an eddy current inspection processing system 44 that includes a processing device 46 and a display device 48. Processing device 46 can be integral with display device 48 or processing device 46 can be separate from display device.

In use, an operator uses inspection device 40 to perform an eddy current inspection of standard 20 (shown in FIG. 2)

to obtain an eddy current signature of standard 20. More specifically, the eddy current signature obtained through the inspection is displayed on display device 48. The operator also performs an eddy current inspection of component 10 (shown in FIG. 1), thus obtaining an eddy current signature of component 10. Through comparison of the eddy current signatures the operator determines if component 10 is structurally sound. In an alternative embodiment, a computer initiates or actuates an eddy current inspection system and determines if component 10 is structurally sound.

Figure 4:
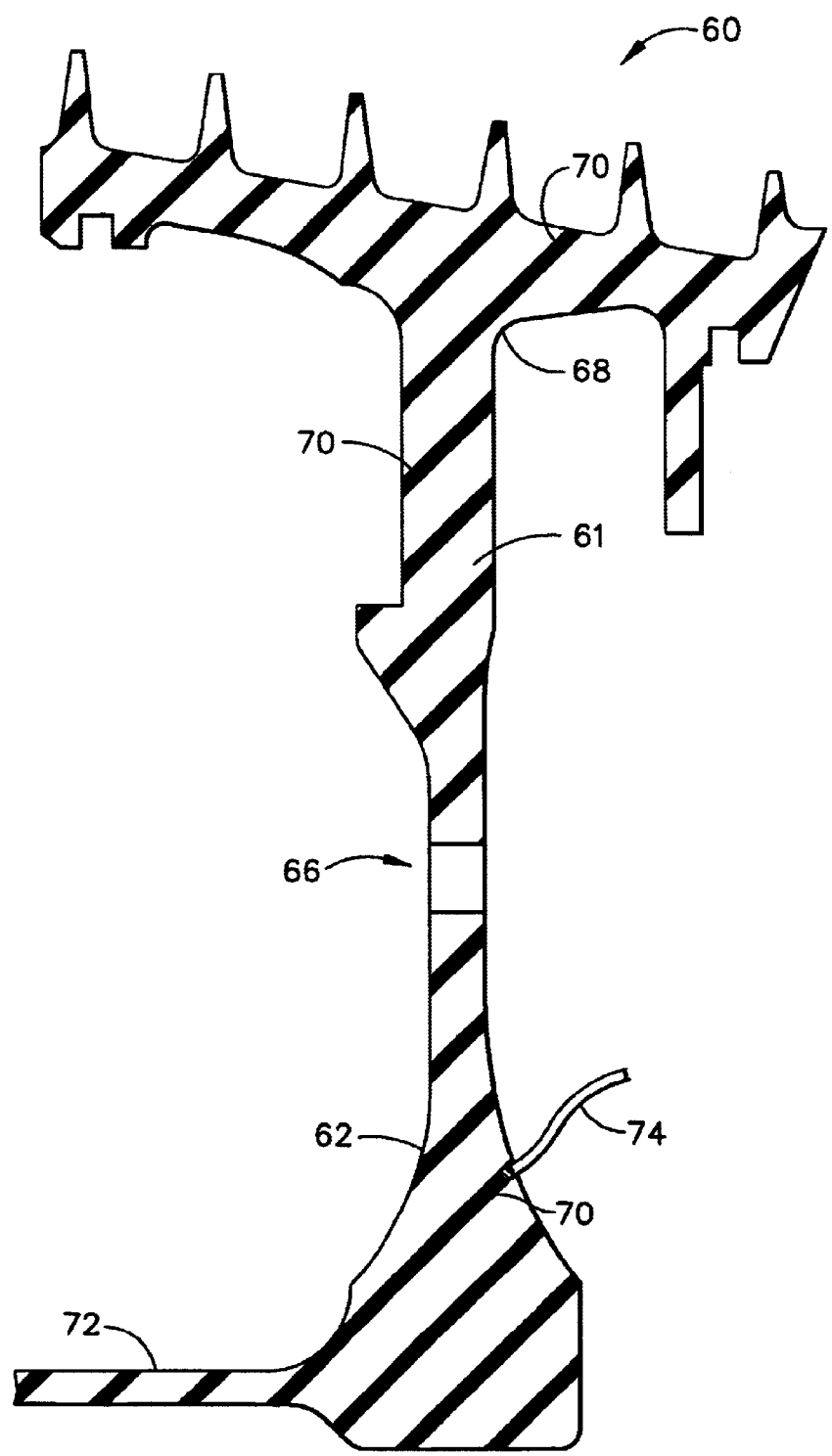
FIG. 4 is a side view of a non-metallic standard.

FIG. 4 is a perspective view of a non-metallic standard 60 including a toroid-shaped non-metallic body 61 that includes at least a plurality of prismatic geometric surfaces and at least one surface 62. Non-metallic standard 60 also includes at least one opening portion 66 and at least one fillet portion 68. Furthermore, non-metallic standard 60 also includes a plurality of grooves 70 extending across an outer surface 72 of body 61. Non-metallic standard 60 and component 10 (shown in FIG. 1) have substantially similarly eddy current signatures. A conductor 74 extends within at least one groove 70 such that non-metallic standard 60 has an eddy current signature that is substantially similar to the eddy current signature of standard 20 (shown in FIG. 2). Accordingly, non-metallic standard 60 has an eddy current signature that is representative of an undamaged and undeteriorated component, i.e., a component that is believed to be structurally sound. In an exemplary embodiment, non-metallic standard 60 and standard 10 are substantially similarly shaped.

Non-metallic standard 60 is fabricated by initially producing a negative mold of standard 20 and then using the negative mold to make a positive non-metallic reproduction. Grooves 70 are then machined into the non-metallic reproduction and, through trial and error, conductors 74 are positioned in grooves 70 until non-metallic standard 60 has an eddy current signature that is substantially similar to the eddy current signature of standard 20. In one embodiment, non-metallic standard 60 is fabricated from an epoxy such as EasyFlo 60® which is commercially available from the Polytek® Development Corporation, 55 Hilton Street, Easton, Pa., 18042 and conductors 74 are thin electrical conducting wires. In an alternative embodiment, non-metallic standard 60 is fabricated from at least one of a polyurethane resin, a polysulfide rubber, a plastic, and a polymer material.

After determining proper placement of conductors 74, the conductors 74 are epoxied in place, and standard 20 is no longer needed and is assembled in a product such as an aircraft engine. Grooves 70 can be straight, arcuate, and may contain both non-arcuate and arcuate portions. Also, grooves 70 may be substantially square-shaped. In one embodiment, grooves 70 are shaped such that at least one groove 70 has at least one line of symmetry. In an alternative embodiment, at least one groove 70 has no lines of symmetry. Additionally, a durometer value for non-metallic standard 60 ranges between Shore 65A to Shore 90D.

In use, an operator uses inspection device 40 to perform an eddy current inspection of non-metallic standard 60 which has an eddy current signature. The eddy current signature obtained through the inspection is displayed on display device 48. The operator also performs an eddy current inspection of component 10 to obtain an eddy current signature of component 10. Through comparison of the eddy current signatures the operator determines if component 10 is structurally sound. In other words, the operator inspects metallic component 10 with reference to inspection standard 60. Additionally, because non-metallic standard 60 is fabricated from an epoxy, non-metallic standard 60 is typically lighter than standard 20, standard 60 facilitates reduced transportation costs and easier handling in comparison to other known standards such as standard 20. Also, as opposed to using standard 20 (which typically is a component that is actually usable in an aircraft) as a reference component, no actual aircraft component is left unassembled, and as such, standard 60 is more cost effective and highly reliable in comparison to standards such as standard 20.

Accordingly, there is provided a method and an inspection standard for eddy current of a metallic component such as an aircraft engine component. The inspection standard is non-metallic and facilities cost savings because it is fabricated from an epoxy and is of lighter weight then the actual component, and may lower transportation costs compared to the costs associated with transporting an actual component (fabricated from a metal) as a standard.

While the invention has been described in terms of various specific embodiments, those skilled in the art will recognize that the invention can be practiced with modification within the spirit and scope of the claims.

What is claimed is:

1. A method for inspecting a metallic component, said method comprising:

providing an inspection standard fabricated from a non-metallic material including at least one conductor and having an eddy current signature substantially similar to an eddy current signature of the metallic component being inspected; and inspecting the metallic component with an eddy current probe with reference to the inspection standard.

2. A method according to claim 1 wherein providing an inspection standard comprises providing an inspection standard including a plurality of grooves that extend across an outer surface of the inspection standard.

3. A method according to claim 2 wherein providing an inspection standard further comprises providing an inspection standard including at least one conductor extending at least partially within at least one of the grooves.

4. A method according to claim 3 wherein providing an inspection standard further comprises providing an inspection standard including at least one conductor that extends within at least one of the grooves such that the inspection standard has an eddy current signature that is representative of an undamaged and undeteriorated metallic component, and wherein inspecting the metallic component comprises inspecting the metallic component by referencing the eddy current signature.

5. A method according to claim 1 wherein providing an inspection standard comprises providing an eddy current inspection standard that has an eddy current signature that is substantially similar to an eddy current signature of an aircraft engine component.

6. A method according to claim 5 wherein providing an inspection standard comprises providing an inspection standard including a plurality of grooves extending across an outer surface of the inspection standard.

7. A method according to claim 6 wherein providing an inspection standard further comprises providing an inspection standard that includes at least one conductor extending within at least one of the grooves such that the inspection standard has an eddy current signature representative of an undamaged and undeteriorated aircraft engine component.

8. A method according to claim 7 wherein said providing an inspection standard further comprises providing an inspection standard fabricated from at least one of an epoxy, polyurethane resin, polysulfide rubber, plastic, and a polymer material.

9. An inspection standard comprising:
   a body fabricated from a non-metallic material and comprising an outer surface
   a plurality of grooves extending across said outer surface; and
   at least one conductor positioned within at least one of said grooves.

10. An inspection standard according to claim 9 wherein said at least one conductor positioned in at least one of said grooves such that said inspection standard has an eddy current signature that is representative of a metallic component having a signature substantially similar to said signature of said inspection standard.

11. An inspection standard according to claim 10 wherein said at least one conductor positioned within at least one of said grooves such that said inspection standard has an eddy current signature that is representative of an aircraft engine component.

12. An inspection standard according to claim 11 wherein said body has a durometer value between 65A and 90D.

13. An inspection standard according to claim 9 wherein said body is fabricated from an epoxy.

14. An inspection device comprising:
    an inspection standard comprising a non-metallic body; and
    an inspection device comprising a probe in close proximity to said inspection standard.

15. An inspection device according to claim 14 wherein said body comprises an outer surface comprising a plurality of grooves extending thereon.

16. An inspection device according to claim 15 further comprising at least one conductor positioned within at least one of said grooves.

17. An inspection device according to claim 16 wherein said body is fabricated from an epoxy.

18. An inspection device according to claim 14 wherein said non-metallic body is fabricated from an epoxy.

19. An inspection device according to claim 18 wherein said probe comprises an eddy current probe, said body has an eddy current signature that is representative of a metallic component that has an eddy current signature substantially similar to said eddy current signature of said standard.

20. An inspection device according to claim 18 wherein said probe comprises an eddy current probe, said body has an eddy current signature that is representative of an aircraft engine component that has an eddy current signature substantially similar to said eddy current signature of said standard.

* * * * *